United States Patent
Seder et al.

(10) Patent No.: US 6,948,526 B2
(45) Date of Patent: Sep. 27, 2005

(54) VALVE MOUNTING ASSEMBLY FOR VOICE PROSTHESIS-CARTRIDGE AND RING

(75) Inventors: Edmund V. Seder, Santa Barbara, CA (US); Tina Porter, Ventura, CA (US)

(73) Assignee: Helix Medical, Inc., Carpinteria, CA (US)

( * ) Notice: Subject to any disclaimer, the term of this patent is extended or adjusted under 35 U.S.C. 154(b) by 0 days.

(21) Appl. No.: 10/487,614

(22) PCT Filed: Dec. 20, 2002

(86) PCT No.: PCT/US02/41274

§ 371 (c)(1),
(2), (4) Date: Feb. 19, 2004

(87) PCT Pub. No.: WO03/057083

PCT Pub. Date: Jul. 17, 2003

(65) Prior Publication Data

US 2004/0187941 A1 Sep. 30, 2004

Related U.S. Application Data

(60) Provisional application No. 60/344,444, filed on Dec. 28, 2001.

(51) Int. Cl.[7] .............................. F16K 15/14; A61F 2/20
(52) U.S. Cl. ........................... 137/855; 137/527; 623/9; 623/11.11; 623/23.68; 623/23.71; 128/207.16
(58) Field of Search ................................. 137/527, 843, 137/855, 269; 623/9, 11.11, 14.11, 23.68, 23.71; 128/207.16

(56) References Cited

U.S. PATENT DOCUMENTS

| | | | | |
|---|---|---|---|---|
| 4,040,428 A | * | 8/1977 | Clifford | 128/207.16 |
| 5,238,749 A | * | 8/1993 | Cueman et al. | 428/441 |
| 5,578,083 A | * | 11/1996 | Laguette et al. | 623/9 |
| 5,632,775 A | * | 5/1997 | Suding et al. | 623/9 |
| 5,957,978 A | * | 9/1999 | Blom | 623/9 |

FOREIGN PATENT DOCUMENTS

DE  197 54 432 A1 * 6/1999

* cited by examiner

*Primary Examiner*—Ramesh Krishnamurthy
(74) *Attorney, Agent, or Firm*—Marvin E. Jacobs

(57) ABSTRACT

The valve mounting system of the invention incorporates a hard cartridge with a grove on its outer, distal surface and a slot communicating distal from the end of the cartridge with the grove and a specially configured elastomeric valve attached to an outer band with a short tab. The band is positioned with the tab aligned with the slot and is stretched and is slid proximally over the cartridge until the tap enters the slot and the band snaps into the seats in the groove. The width of the slot is the same as the width of the tab providing exact alignment of the valve element with the seat provided in the cartridge. The tab can be disposed at an angle to the seat to preload the valve element against the seat.

23 Claims, 4 Drawing Sheets

VALVE MOUNTING ASSEMBLY FOR VOICE PROSTHESIS-CARTRIDGE AND RING

This application claims the benefit of Provisional Application No. 60/344,444 filed Dec. 28, 2001.

TECHNICAL FIELD

This invention relates to a voice prosthesis and more particularly this invention relates to a mounting assembly for a valve.

BACKGROUND OF THE INVENTION

There are several options for restoring speech to patients who have had their larynx removed. One procedure is to surgically create a puncture or fistula between the tracheal and the esophagus. A trachea voice prosthesis containing a one-way valve such as a BLOM-SINGER® voice prosthesis is inserted into the trachea-esophageal fistula. The one-way valve protects the airway during swallowing but opens under positive pressure. The voice prosthesis, thus, permits a patient to divert air from the lungs into the esophagus and out through the mouth. Speech is created during passage of air through the upper part of the esophagus.

The prosthesis maintains the fistula open, transfers air from the trachea to the esophagus for voice production and prevents esophageal leakage into the trachea during swallowing. However, the prosthesis being in contact with moisture in a hot, dark environment is subject to growth of commonly found yeast formation, typically Candida Albicans on the valve and the retaining flange. The growth of yeast can interfere with function of the valve and can cause the flange to wrinkle and leak.

The current low pressure voice prosthesis can be removed by the patient every few days and can be replaced with a clean prosthesis. The removed prosthesis is soaked in hydrogen peroxide to remove the layer of yeast from the valve and flange. Some patients such as quadriplegic patients or patients suffering from neurological conditions such as Multiple Sclerosis have difficulty managing frequent removal and reinsertion of the prosthesis. Others, who are physically handicapped are not able to remove, sterilize, or reinsert the prosthesis.

A longer dwelling, low pressure voice prosthesis has been developed that can remain in place in the trachea-esophageal fistula for over 3–4 days, depending on the patient and conditions of use. The patient can confidently use the prosthesis for longer periods. Trips to a health care specialist to remove and replace the prosthesis are greatly extended providing increased comfort and lower cost to the patient.

The flange or collar that rests against the tracheaesophageal wall is strengthened by increasing the thickness and/or diameter of the flange. The stronger flange is more resistant to wrinkling or detachment from the wall. The voice prosthesis can remain in place in the fistula for much longer periods without allowing leakage between the trachea and the esophagus. The stronger and larger collar also reduces possibility of dislodgement of the prosthesis during a coughing or sneezing episode. However, the thicker and wider flange is more difficult to insert through the fistula and does not reliably seat on the trachea-esophageal wall.

Yeast growth on the valve can also cause distortion of the shape of the valve or form wrinkles in the body of the valve which prevents the valve from closing.

Leaking also appears to be due to distortion of the valve body adjacent to the seat of the valve and to yeast growth on the seat. Forming the valve with an arcuate dome shape increased resistance to folding or bending of the valve. However, some valves still leaked after extended placement in a fistula.

LIST OF REFERENCES

U.S. Pat. No. 5,314,470
U.S. Pat. No. 5,578,803
U.S. Pat. No. 5,480,432

STATEMENT OF THE PRIOR ART

U.S. Pat. No. 5,314,470 discloses a soft voice prosthesis which includes a stiffening ring 14 inserted into a groove in the body of the prosthesis. Though the ring stiffens the body adjacent the valve does not prevent distortion of the body by muscular movement or distortion of the valve by growth of yeast. The valve is thin, it is not dome shaped and is not pre-loaded. It will readily distort when a layer of yeast grows on its surface. Furthermore, the flap valve is attached to the soft body with a segment that remains after cutting the valve from the body. This is a labor intensive step and the thin segment does not provide a secure and reliable attachment of the valve to the prosthesis. If the segment should sever, the valve could fall into the lungs of the user.

U.S. Pat. No. 5,578,083 issued Nov. 26, 1996 discloses the use of a rigid cartridge. The cartridge prevents distortion of the soft body of the prosthesis. The valve contains a mounting tab normal to the body of the valve which is potted into a slot in the cartridge. The valve and cartridge are very small, especially the tab and slot. They are difficult to manipulate. Correct seating of the tab in the slot is not reliable resulting in a high percentage of prosthesis in which the valve does not seal when in the closed position and must be discarded.

STATEMENT OF THE INVENTION

The valve mounting system of the invention is easy to manipulate and install. The valve mounting system reliably seats the valve in correct position. Adhesive is not necessary to achieve reliable and long term functioning of the valve. The valve mounting system of the invention incorporates a hard cartridge with a groove on its outer, distal surface and a slot communicating distal from the end of the cartridge with the groove and a specially configured elastomeric valve attached to an outer band with a short tab. The band is positioned with the tab designed with the slot and is stretched and slid proximally over the cartridge until the tab enters the slot and the band snaps into and seats in the groove. The width of the slot is the same as the width of the tab providing exact alignment of the valve element with the seat provided in the cartridge. The tab can be disposed at an angle to the seat to preload the valve element against the seat.

The cartridge-valve assembly is then inserted into a recess provided in the channel of the soft body of a voice prosthesis. The cartridge and valve are not in direct contact with tissue and can contain antimicrobial agents to prevent or retard growth of microbial films.

The valve may optionally be dome-shaped to provide further strengthening of the valve and to assure that it will not distort and leak even when encrusted with a layer of yeast.

These and many other features and attendant advantages of the invention will become apparent as the invention becomes better understood by reference to the following detailed description when considered in conjunction with the accompanying drawings.

DETAILED DESCRIPTION OF THE INVENTION

Figure 1:
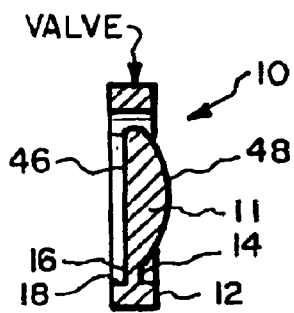
FIG. 1 is a view in section of a valve with seating band according to the invention.
Figure 3:
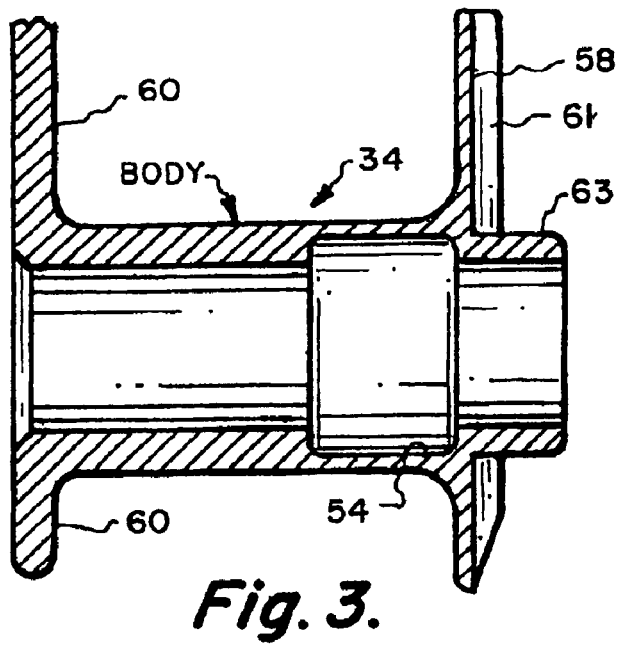
FIG. 3 is a view in section of a soft body for a voice prosthesis according to the invention.
Figure 2:
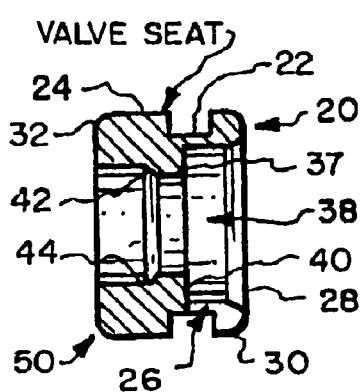
FIG. 2 is a view in section of a hard cartridge with valve seat according to the invention.
Figure 4:
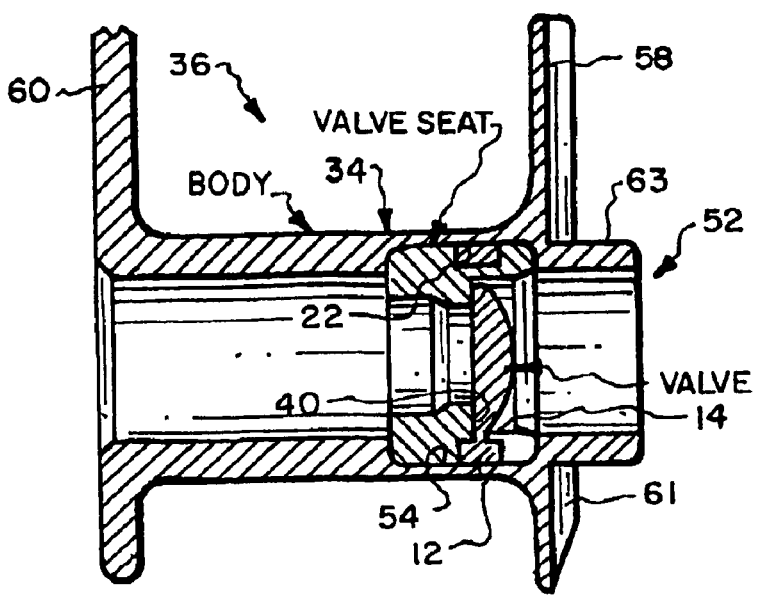
FIG. 4 is a view in section of the assembly of the body, cartridge and valve illustrated in FIGS. 1–3.

Referring now to FIGS. 1–4, FIG. 1 illustrates an elastomer flapper valve 10 formed of a valve element 11 spaced from and connected to a surrounding mounting band 12 by a tab 14 extending from the outer surface 16 of the valve element to inner surface 18 of the band 12. The rigid cartridge 20 shown in FIG. 2 has a groove 22 formed in the outer surface 24 and a slot 26 formed in the distal surface 28 extending from the distal surface 28 to the groove 22. The width of the slot 26 is coextensive with the width of the tab 14. The outer edges of the distal surface 28 is rounded at 30 to prevent tearing of the mounting band 12 as it is assembled with the cartridge 20. The outer edge 32 of the proximal surface of the cartridge 20 can also be chamfered or rounded to prevent tearing of the soft body 34 of the voice prosthesis 36.

Figure 9:
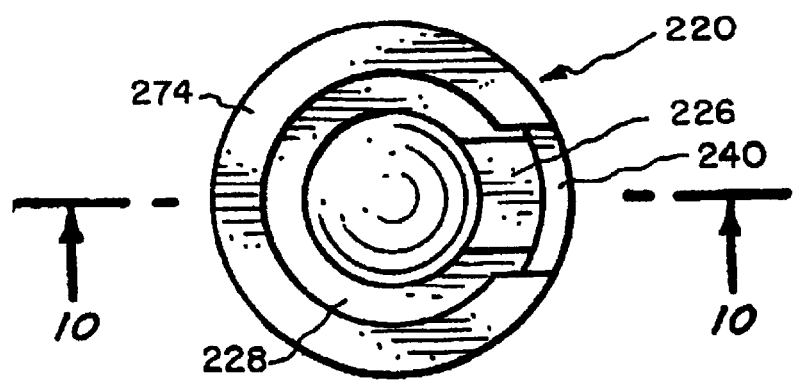
FIG. 9 is a top view in elevation of the cartridge illustrated in FIG. 8.

The cartridge 20 contains a boss 37 extending into the channel 38 through the cartridge forming on its distal surface a seat 40 for the valve element 11. The seat 40 can be disposed normal to the axis of the channel or can be slanted at an angle of 5–10 degrees as illustrated in FIG. 9. The proximal face 42 of the boss 37 can be utilized to engage the distal end of a cleaning brush or insertion tool. The edge 44 of the proximal face 42 can be chamfered.

Referring again to FIGS. 1 to 4 the voice prosthesis 36 is assembled by stretching the band 12 while aligning the tab 14 with the slot 26. The stretched band 12 is then placed over the groove 22 while the tab 14 is seated in the slot 26 against the seat 40 and released into the groove 22. The proximal face 46 of the valve element 11 is reliably seated against the valve seat 40. The valve element 11 may have a dome shape 48 to strengthen the element and prevent wrinkling of the element.

The cartridge-valve assembly 50 is then pushed through the distal end 52 of the soft body 34 until it seats in the annular recess 54 within the soft body 34. The soft body 34 can also contain a conventional distal flange 58 and proximal flange 60 for engaging the surfaces of wall between a trachea and esophagus. The distal flange 60 can contain a radioplaque ring 61 in order to assure that the flange 60 is correctly seated as disclosed in Ser. No. 08/282,277 filed Jul. 27, 1994 now issued as U.S. Pat. No. 5,480,432, the disclosure of which is expressly incorporated herein by reference. The soft body 34 can contain a distal hood 63 to further protect the valve element 1 from being fouled.

Figure 5:
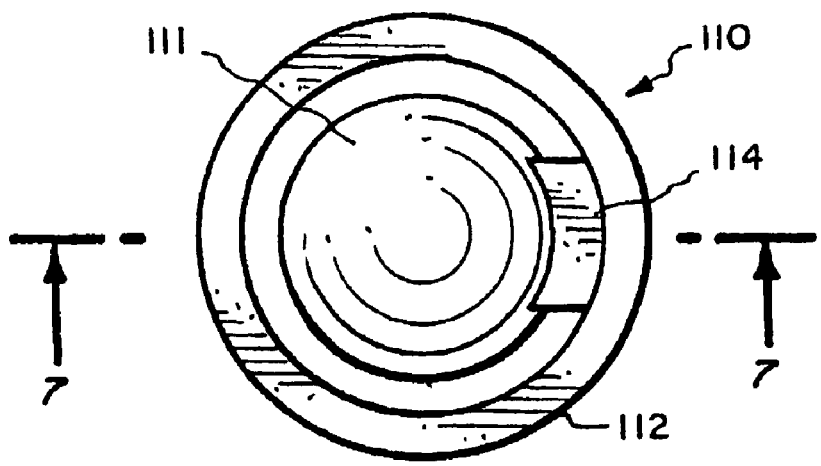
FIG. 5 is a top view in elevation of an alternate embodiment of a valve.
Figure 6:
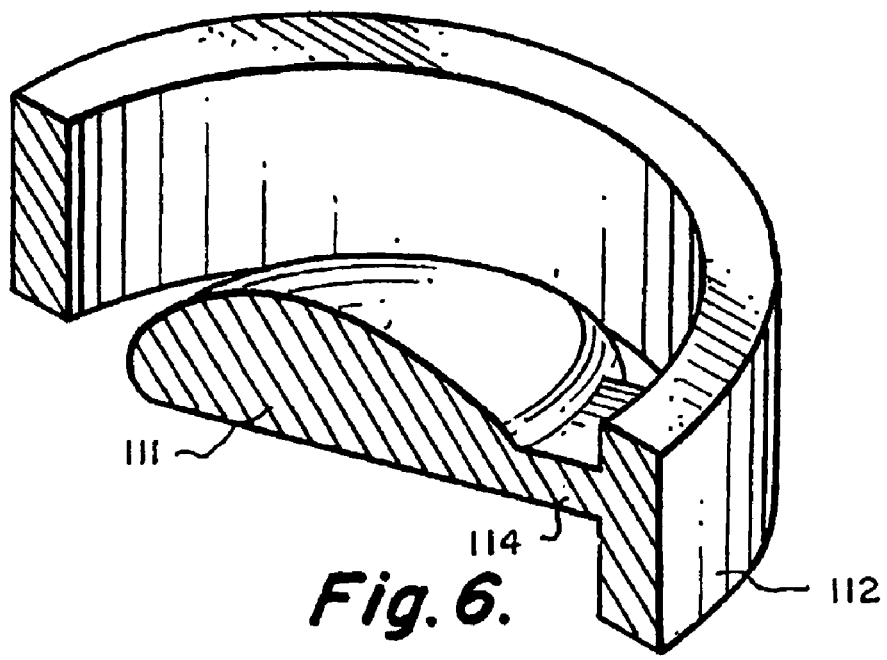
FIG. 6 is a perspective and sectional view of the valve illustrated in FIG. 5.
Figure 7:
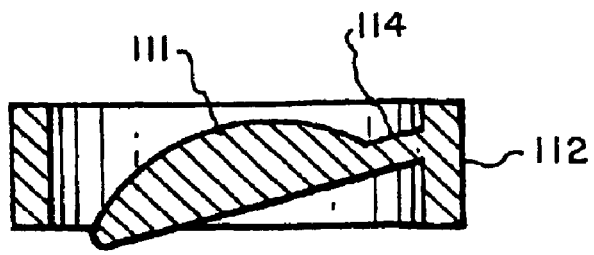
FIG. 7 is a view in section taken along lines 7—7 of FIG. 6.

Referring now to FIGS. 5–7, an alternate embodiment of a valve 110 can be preloaded by forming the tab 114 at an angle from 5 to 20% to a plane normal to the axis of the mounting band 112. The valve element 111 will preload when assembled with a cartridge, not shown.

Figure 8:
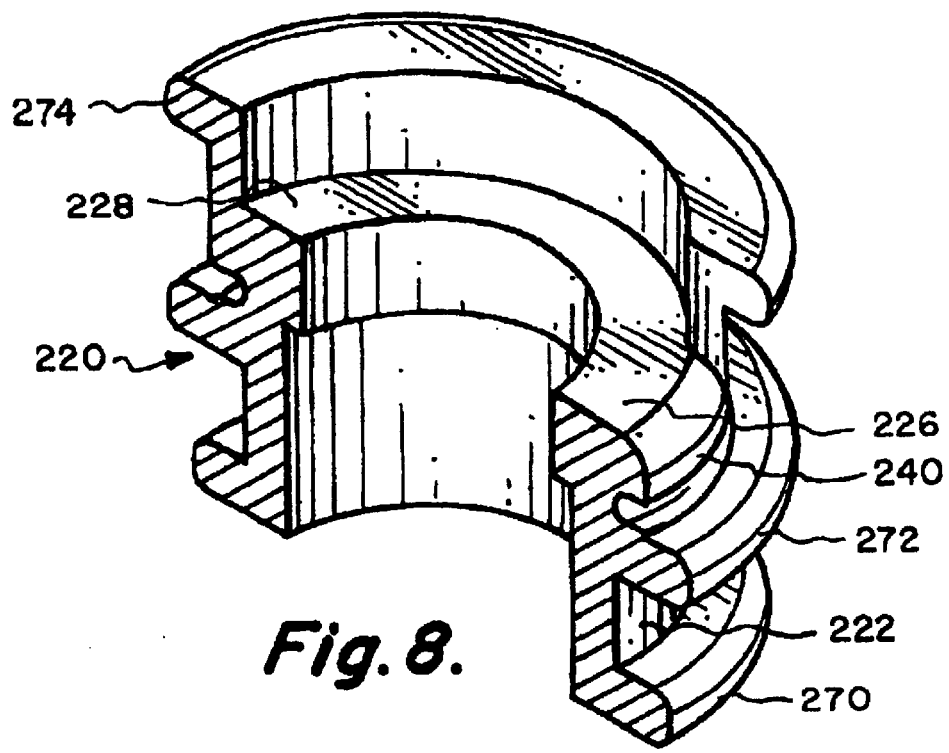
FIG. 8 is a perspective view of an alternate embodiment of a cartridge.
Figure 10:
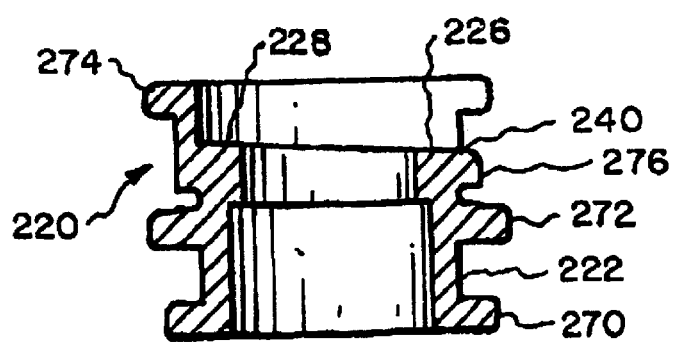
FIG. 10 is a view in section taken along lines 10—10 of FIG. 9.

Referring now to FIGS. 8–10, another way to preload a valve element, not shown, is to form the seating face 240 of a-cartridge 220 at an angle of 5–20 degrees by disposing the face 240 at the slot 226 forward of the opposed face 228. The cartridge 220 illustrated in FIGS. 8-10 contains three flanges, a proximal flange 270, a central flange 272 and a distal flange 274 forming a first groove 222 between flanges 272 and 274 for receiving a mounting band of a valve, not shown and a second groove 276 for receiving a cylindrical boss on the body of a prosthesis, not shown, for better securing the assembly of the soft body and the cartridge 220.

Figure 11:
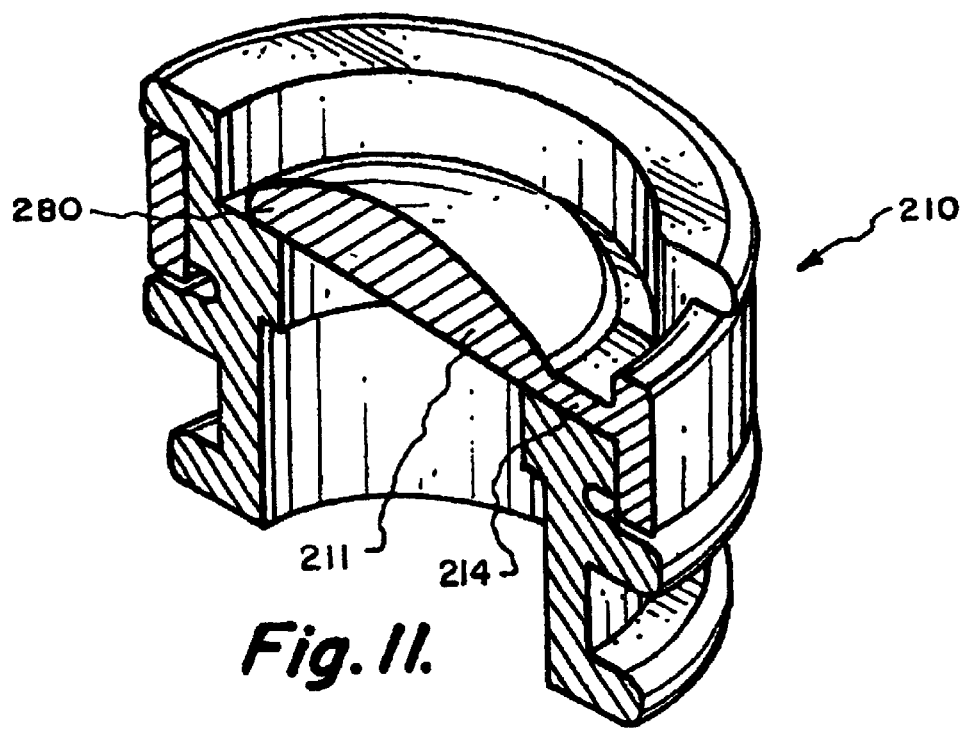
FIG. 11 is a perspective sectional view of the assembly of a valve with the cartridge illustrated in FIG. 8.
Figure 12:
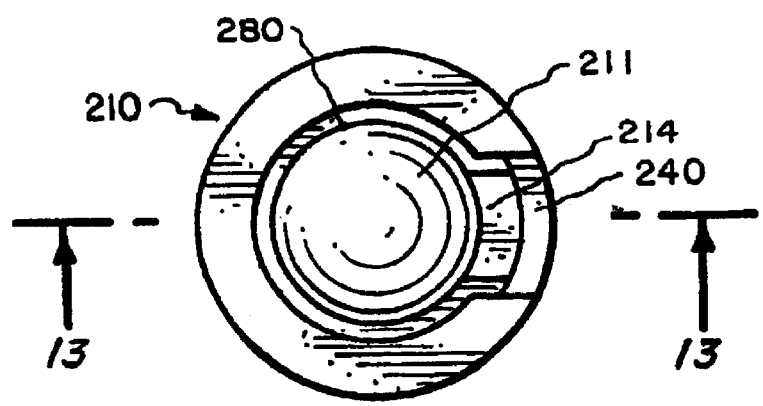
FIG. 12 is a top view in elevation of the assembly illustrated in FIG. 11.
Figure 13:
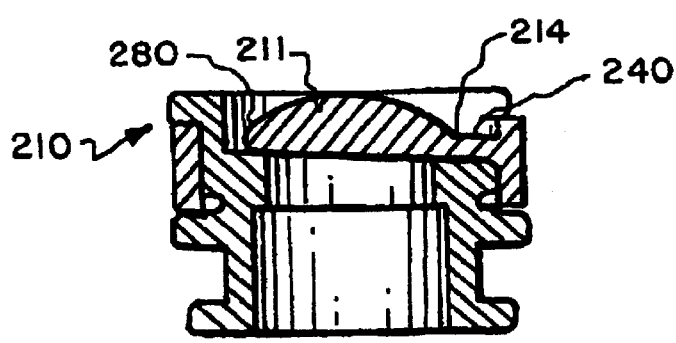
FIG. 13 is a view in sections taken along lines 13—13 of FIG. 12.

Referring now to FIGS. 11–13 a valve 210 is illustrated assembled with the cartridge 220. The edge portion 280 of the valve element 211 opposite the tab 214 is preloaded by being faced rearwardly by the slanted seating surface 240.

The Indwelling Low Pressure Voice Prosthesis of the invention is designed for those persons who are unable or resistant to changing the voice prosthesis every two or three days as was recommended for the non-indwelling, patient-removable Low Pressure Voice Prosthesis. The Indwelling Low Pressure Voice Prosthesis has been specifically designed to maintain the placement of the prosthesis in the trachea-esophageal puncture so that routine changing of the device is not necessary.

The Indwelling Low Pressure Voice Prosthesis is loaded into a gelatin capsule, using a gel cap loading tool. The gel cap provides a smooth, rounded shape to the tip end of the voice prosthesis, thus enabling easier entry into the trachea-esophageal puncture when placed by the clinician.

The prosthesis is placed in the fistula by inserting the strap of the voice prosthesis into the center hole on the top side of the gel cap loading tool and gently pulling the prosthesis down and through this opening until the rear esophageal flange is positioned over this center hole.

The tubular portion of the voice prosthesis is grasped and the prosthesis is very slowly pulled down further, such that the rear flange on the tip of the voice prosthesis begins to fold forward inside the center hole. Over-pulling will cause the voice prosthesis to be pulled completely through the loading device. The gel cap is placed over the center hole in the loading tool and into the groove, such that it is securely in place. A fingertip is placed on the tip of the gel cap while simultaneously pushing the voice prosthesis back up through the center hole and out of the loading device. The prosthesis is pushed, gently until the folded, rear flange is fully residing in the gel cap. The pushrod provided with the gel cap loading tool may be used to push the device through from the back.

The gel cap-tipped end of the voice prosthesis is gently grasped and the prosthesis is carefully pulled the rest of the way back up through the loading device. The prosthesis is placed on the inserter, and the strap attached over the safety peg, as shown in U.S. Pat. No. 5,064,433, the disclosure of which is expressly incorporated herein by reference. The position of the gel cap on the tip of the voice prosthesis is inspected to assure that it is securely and fully encapsulating the rear flange.

A light coating of water or water-soluble lubricant (oil-free) is applied to the tip of the gel-capped end of the voice prosthesis and the voice prosthesis is immediately inserted fully into the trachea-esophageal puncture by aligning the tip of the voice prosthesis partially in the puncture with the neck strap oriented upwards. The prosthesis is held in this position of full insertion for at least 3 minutes. This allows time for the gel cap to dissolve and release the retention collar within the esophagus.

If the prosthesis does not insert easily on the first attempt, do not continue to try to insert. Instead, a clean 22 French trachea-esophageal dilator is inserted for a few minutes to dilate the pathway.

The voice prosthesis strap is detached from the safety peg on the inserter. A finger is placed against the strap and the inserter is carefully withdrawn from the prosthesis with a twisting motion. A piece of tape is placed over the voice prosthesis strap against the skin.

The Indwelling Low Pressure Voice Prosthesis of the invention is designed to permit optional detachment of the strap by a physician or trained speech pathologist following confirmation that the rear flange on the prosthesis is fully opened and securely positioned.

The rear flange emerges from the dissolved gel cap and unfurls within the esophageal lumen. Seating of the rear flange against the anterior wall of the esophagus, can be confirmed by rotating the inserted prosthesis within the puncture while it is attached to the inserter. A correctly and securely inserted prosthesis will rotate freely. Rotate the prosthesis repeatedly 360°. Slight resistance may be detected on the first rotation because of residual gelatin that has not completely dissolved. Allow at lest three minutes for the gel cap to dissolve following prosthesis insertion before proceeding with the rotation confirmation procedure. A voice prosthesis that does not rotate freely suggests that the rear flange has not unfurled and seated within the esophageal lumen. Assessment of the position of the rear flange of the prosthesis is recommended for direct confirmation/assessment.

Removal of the Indwelling Low Pressure Voice Prosthesis should only be done by grasping the outer rim of the device securely with a hemostat. Pull gently and firmly until the prosthesis is fully withdrawn. Insert a 22 French dilator and tape it into position for five minutes prior to inserting a new Indwelling Low Pressure Voice Prosthesis that has been attached to an inserter. Never remove one voice prosthesis and reinsert another voice prosthesis without first dilating the trachea-esophageal puncture with the 22 French dilator. Always use a gel cap on the tip of an Indwelling Low Pressure Voice Prosthesis to enable easy, atraumatic insertion.

The Indwelling Voice Prosthesis may be left in place in the trachea-esophageal puncture until it ceases to function correctly, that is, until it leaks or is not providing adequate voice for speech. If the prosthesis is not functioning properly, the patient should return to the clinician for evaluation.

The Blom-Singer Flushing Pipet provides a means for flushing small particulate matter from the lumen and valve member of the Blom-Singer Indwelling Low Pressure Voice Prosthesis while in-situ, i.e., in the user's trachea-esophageal puncture. The following instructions should be made clear to the patient as part of the routine care of the Blom-Singer Indwelling Low Pressure Voice Prosthesis.

The patient should illuminate the tracheostoma with a bright light source such that the open end of the voice prosthesis is clearly visible. Use long handled forceps (tweezers) to carefully remove any dried debris (phlegm) that may be in the open end of the voice prosthesis.

Fill approximately one third of the stem of the pipet with clean water. Carefully and gently insert the tip of the pipet into the voice prosthesis only until it abuts against the stopper on the stem of the pipet. Briskly squeeze the bulb on the pipet to flush a rapid squirt of water through the voice prosthesis. If liquid will not readily squirt through the voice prosthesis, this indicates that it may be plugged with dried phlegm. Allow a few drops of water to dissolve this dried matter for a few minutes and then re-flush with the pipet until the debris breaks free. The debris must be removed from the trachea-esophageal puncture with a hemostat by the clinician for -thorough cleaning. Never attempt to reinsert an Indwelling Low Pressure Voice Prosthesis that has the strap removed.

After flushing, remove the pipet carefully to avoid dislodging the voice prosthesis. Inspect the interior of the voice prosthesis with a bright light. Repeat flushing as needed.

If the voice prosthesis is accidentally dislodged from the puncture, the patient should be instructed to immediately place a 22 French dilator in the puncture to keep the puncture from closing. The patient should then return to his/her clinician for re-insertion of the voice prosthesis.

It is to be realized that only preferred embodiments of the invention have been described and that numerous substitutions, modifications and alterations are permissible without departing from the spirit and scope of the invention as defined in the following claims.

What is claimed is:

1. A cartridge for mounting a flapper valve for a voice prosthesis comprising in combination;
    a hollow, rigid tubular member having a tracheal end and an esophageal end;
    a first flange mounted on the outer surface of the tubular member at the tracheal end;
    a second flange mounted on the outer surface of the member at the esophageal end;
    a third flange mounted on the outer surface of the tubular member between the first and second flanges forming a first groove between the first and third flanges for receiving a boss projecting from an inner surface of a soft prosthesis body and the second and third flanges forming a second groove for receiving a mounting band of the flapper valve.

2. An assembly of a cartridge and valve for a voice prosthesis comprising in combination;
    an elastomeric valve having a valve flap connected to an outer cylindrical mounting band by a hinge segment; and
    a rigid cartridge having a hollow body with an outer groove for receiving said band and segment of the distal portion of the body communicating the distal end of the body with the groove for receiving the hinge segment of the valve flap.

3. A voice prosthesis comprising in combination;
    a soft, elastomeric, hollow voice prosthesis body having a wall connecting a tracheal end and an esophageal end;

a cylindrical recess in the internal surface of the wall; and a cartridge-valve assembly as defined in claim 2 received in said recess.

4. A voice prosthesis according to claim 3 in which the body further includes a tracheal flange and an esophageal flange.

5. A voice prosthesis according to claim 4 in which the esophageal flange is mounted forward of the esophageal end of the body forming a hood extending rearward of the valve.

6. A flapper valve for mounting across the open end of a tubular voice prosthesis comprising in combination;

a round valve flap having a first diameter and an outer edge;

a discrete outer, continuous cylindrical mounting band having a front edge and a rear edge, an inner surface and an inner second diameter larger than the first diameter of the valve flap forming an annular space between the inner surface of the mounting band and the outer edge of the valve flap;

a hinge segment disposed in said annular space connected to a portion of the outer edge of the valve flap in a plane substantially parallel to the valve flap and connected to a portion of the inner surface of the mounting band between the front and rear edges of the mounting band positioning the remainder of the outer edge of the valve flap spaced from the inner surface of the mounting band.

7. A flapper valve according to claim 6 formed of a medical grade elastomer in which the valve portion, hinge segment and mounting band form a unitary structure.

8. A flapper valve according to claim 7 in which the valve flap has a front face with a flat seating surface.

9. A flapper valve according to claim 8 in which the valve flap has a dome-shaped rear surface.

10. A flapper valve according to claim 6 in which the hinge segment is no more than 10 percent of the circumference of the valve flap.

11. A flapper valve according to claim 10 in which the hinge segment has a thickness less than the thickness of the valve flap.

12. A flapper valve according to claim 6 in which the elastomer contains an antimicrobial agent in an amount effective to retard microbial growth.

13. A flapper valve according to claim 6 in which the mounting band is circular, has a rectangular cross-section and is centrally disposed between the front and rear edges of the mounting band.

14. A cartridge according to claim 13 in which the outer surface of the wall contains a second groove forward of the first groove for receiving an anterior boss projecting from the inner surface of the soft body of a voice prosthesis.

15. A cartridge according to claim 14 in which the outer wall of the tubular member is connected to a tracheal flange, and esophageal flange and a central flanges, said first groove is formed between the central flanges and the esophageal flange and the second groove is formed between the tracheal flange and the central flange.

16. A hard cartridge for mounting a soft elastomeric valve assembly in the body of a soft, elastomeric voice prosthesis, said valve assembly including a round flap connected to the inner surface of a soft mounting band having a first length by a segment parallel to the flap forming an annular space between the outer edge of the flap and the inner surface of the mounting band, said cartridge comprising in combination;

a hollow, rigid tubular member having an annular wall connecting a tracheal face to an esophageal face, the wall having an outside and an inside surface;

a first groove having a length about the same as the length of the mounting band formed in the outer surface of the tubular member for receiving the mounting band with the valve flap disposed within the tubular member;

an opening in the esophageal face of the tubular member extending to said groove for the passage of the connecting segment of the valve assembly into the groove.

17. A cartridge according to claim 16 in which the cartridge is cylindrical.

18. A cartridge according to claim 17 in which the outer peripheral edges of the faces are rounded or chamfered.

19. A cartridge according to claim 17 in which the groove has a rectangular cross-section.

20. A cartridge according to claim 16 in which the inner surface of the annular wall contains an interior boss having an esophageal facing surface for sealing the edge of a flapper probe.

21. A cartridge according to claim 20 in which the seating surface is disposed at an angle to a plane perpendicular to the axis of the cartridge.

22. A cartridge according to claim 21 in which the angle is no more than 10 degrees.

23. A cartridge according to claim 20 in which the boss has a tracheal facing surface for receiving the distal end of an insertion tool or of the end of a body of a cleaning too.

* * * * *